United States Patent [19]

Kepler

[11] Patent Number: 5,347,845
[45] Date of Patent: Sep. 20, 1994

[54] APPLIANCE SHIPPING CONTAINER AIR SAMPLING SYSTEM

[75] Inventor: Robert P. Kepler, Crawford County, Ark.

[73] Assignee: Whirlpool Corporation, Benton Harbor, Mich.

[21] Appl. No.: 19,483

[22] Filed: Feb. 19, 1993

[51] Int. Cl.⁵ .............................................. G01N 1/24
[52] U.S. Cl. ........................................ 73/31.03; 73/52; 73/863.01; 73/864.21; 73/864.74; 73/864.81; 209/552
[58] Field of Search ................... 73/23.2, 31.03, 40, 73/41, 40.7, 45, 45.1, 863, 863.81, 863.91, 864.81, 864.74, 864.21, 52; 206/320, 459.1, 459.5; 209/552, 559, 560, 591

[56] References Cited

U.S. PATENT DOCUMENTS

| | | | |
|---|---|---|---|
| 2,169,605 | 8/1939 | Griese | 23/232 |
| 3,520,176 | 7/1970 | Becker | 73/40.7 |
| 3,723,713 | 3/1973 | Banner et al. | 235/151.35 |
| 4,436,998 | 3/1984 | Tallon | 250/288 |
| 4,711,096 | 12/1987 | Krantz | 62/129 |
| 4,758,366 | 7/1988 | Parekh | 252/68 |
| 4,879,546 | 11/1989 | Dunham et al. | 340/632 |
| 5,060,529 | 10/1991 | Bals et al. | 73/864.74 |
| 5,099,679 | 3/1992 | Huerlimann et al. | 73/52 |
| 5,198,774 | 3/1993 | Williams, II et al. | 324/464 |
| 5,212,993 | 5/1993 | Mayer | 73/864.21 |

Primary Examiner—Hezron E. Williams
Assistant Examiner—Michael J. Brock
Attorney, Agent, or Firm—Joel M. Van Winkle; Thomas J. Roth; Stephen D. Krefman

[57] ABSTRACT

A system for sampling air contained in an appliance shipping container includes a gas analyzer sealably interconnected with a probe by a flexible conduit. Disposed on the lower portion of a side wall of the appliance shipping container is an opening sealably covered by a film patch. A conveyor line arrangement positions the shipping container such that the film patch is disposed adjacent the probe. When the appliance shipping container is detected to be suitably positioned adjacent the probe, an electro-solenoid interconnected with the probe is activated causing the probe to puncture the reflective film patch and permitting an air sample to be drawn from the appliance shipping container into the gas analyzer. If the presence of a vaporized refrigerant is detected, a controller shunts the appliance shipping container to a site for repair of the appliance.

17 Claims, 3 Drawing Sheets

APPLIANCE SHIPPING CONTAINER AIR SAMPLING SYSTEM

BACKGROUND OF THE INVENTION

The present invention is directed to a system for sampling the air within an appliance shipping container and detecting the presence of contaminants in the air, and more particularly to a system for detecting a refrigerant leak from a refrigerator disposed within a shipping container.

Typically, an appliance such as an air conditioner, freezer or a refrigerator includes a refrigeration system having a compressor, evaporator and condenser sealably connected together and having a charge of pressurized refrigerant. More specifically, in the manufacture of refrigerator appliances, it is well known that leaks of refrigerant from the refrigeration system may cause the refrigerator to fail to operate. Further, the leaks in the refrigeration system may be of a very minute nature and accordingly are difficult to detect because the refrigerant used in most modern appliances is odorless and colorless.

Various methods are used therefore, for detecting leaks in the refrigeration system of the refrigerator during the manufacturing process of the refrigerator. For example, one such method includes submerging a portion of the refrigeration system, pressurized with compressed air, in a liquid bath and visually noting the presence of bubbles which indicate the presence of leaks. Another method involves pressurizing a portion or all of the refrigeration system using compressed air and monitoring the system for any loss of pressure which would indicate a leak.

Typically, the above mentioned leak detection methods are employed to identify leaks in the components of the refrigeration system and their interconnections prior to charging the system with refrigerant. However, leaks may develop in the refrigeration system after installation of the refrigeration system into the refrigerator cabinet structure and after the refrigeration system has been charged with refrigerant. These leaks may be due to damage which occurs during subsequent assembly and packaging steps of the refrigerator after the installation of the refrigeration system and handling of the refrigerator once it is in the shipping container.

It would be desirable, therefore, to develop a system for detecting leaks in a refrigeration system of a refrigerator upon the completion of the manufacturing process of the refrigerator. Such a system is made difficult by the fact that the typical refrigerant used in a refrigeration system is similar to the typical blowing agents used for providing foam insulation in the refrigerator. Therefore, leak detection equipment must be able to discriminate between refrigerant compounds and blowing agent compounds. Furthermore, a leak in the refrigeration system, which occurs after the system has been charged with refrigerant, will allow the refrigerant to leak from the system in a gaseous form and unless confined, the gaseous refrigerant will quickly disperse. A novel solution for detecting leaks in a refrigeration system may be found, however, by utilizing the shipping container surrounding the refrigerator as an enclosure for partially confining leaking refrigerant from the refrigeration system such that a novel method to detect leaks in a refrigeration system may operate by detecting the presence of the refrigerant as an air contaminant within the shipping container.

SUMMARY OF THE INVENTION

In accordance with the present invention, the disadvantages of prior art leak detection systems have been overcome by utilizing a system for detecting the presence of a leak in a sealed refrigeration system of an appliance, such as a refrigerator. During the final steps of the manufacturing process, a cardboard shipping container is placed over the refrigerator. The system is configured to detect leaks in a refrigerator which is contained in such a shipping container. The shipping container includes a plurality of side walls, each of which has an upper portion and a lower portion. Disposed on the lower portion of a side wall of the shipping container is an opening sealably covered by a film patch. The system further includes a probe having an internal conduit and a means for positioning the bottom portion of the shipping container containing the refrigerator such that the film patch is disposed in front of the probe. A sensor is provided for verifying the presence of the film patch in front of the probe. An electrosolenoid actuator is provided for forcibly inserting the probe through the film patch. An air contaminant detection apparatus is interconnected with the probe such that a test sample of air from within the shipping container may be admitted to the air contaminant detection apparatus. A means for indicating the presence of a contaminant is further provided along with an apparatus for sorting the shipping container containing a refrigerator in response to a presence of the contaminant.

Accordingly, an object of the present invention is to detect the presence of contaminants in the air contained in a shipping container.

Another object of the present invention is to detect leaks in a refrigeration system of a refrigerator upon completion of the manufacturing process of the refrigerator when the refrigerator is disposed in a shipping container.

Still another object of the present invention is to provide a shipping container having an opening sealably covered by a film patch such that penetration of a probe through said film patch may be obtained.

DETAILED DESCRIPTION OF THE PREFERRED EMBODIMENT

Figure 1:
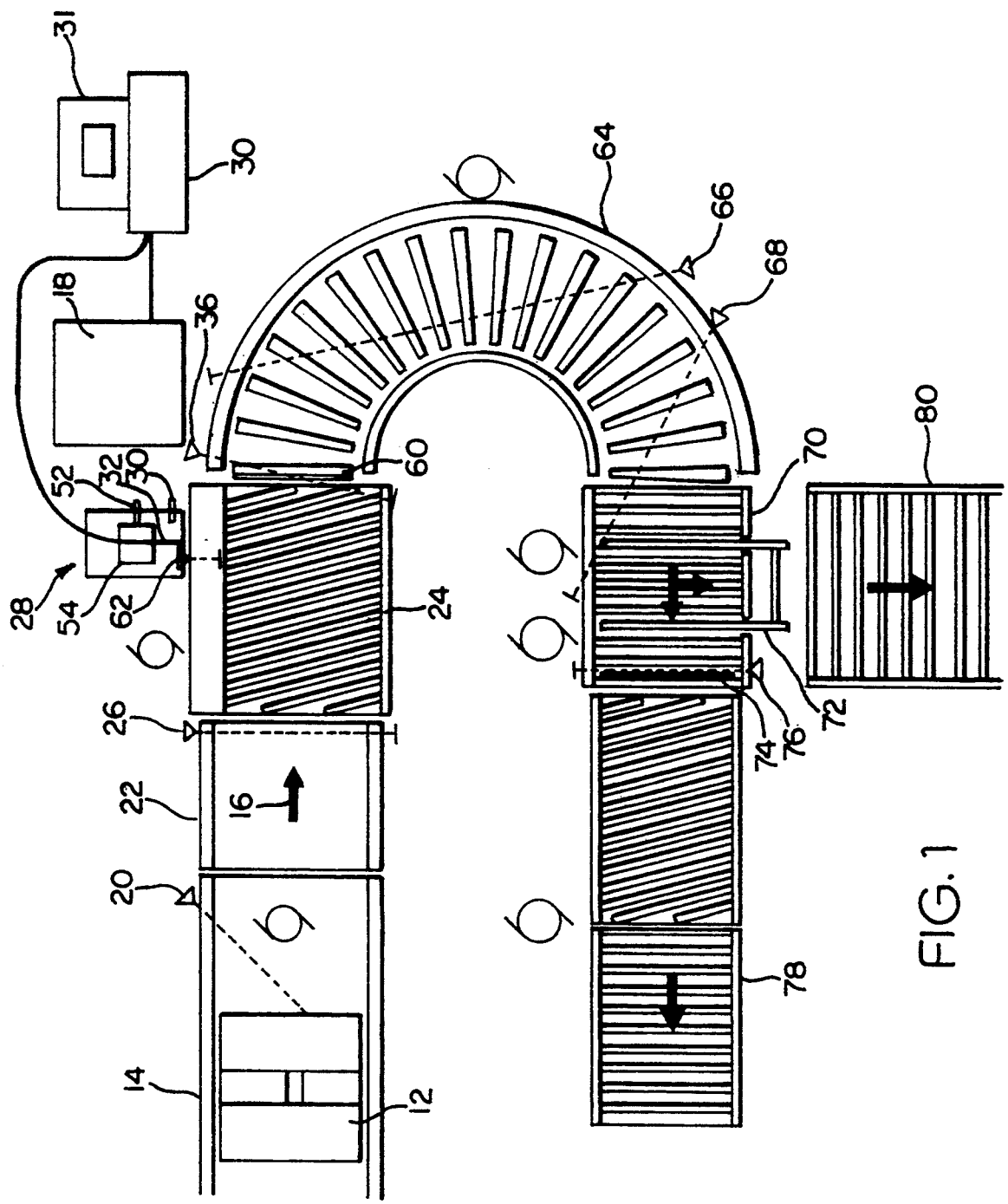
FIG. 1 is a top plan view of a manufacturing conveyor system in accordance with the present invention.

Referring now to the drawings and more particularly FIG. 1, there is shown a schematic diagram of a portion of a manufacturing conveyor line which will be readily understood by those skilled in the art. Typically, upon completion of all manufacturing steps of a refrigerator, the refrigerators are conveyed from a manufacturing area to a distribution area for eventual shipment to retail stores. As contemplated by the inventor, the portion of conveyor line shown in FIG. 1 represents the end portion of a conveyor line for conveying a completed refrigerator surrounded by a shipping container to the distribution area from the manufacturing area.

In accordance with the invention as shown in the FIG. 1, therefore, a shipping container 12 contains an appliance such as a refrigerator (not shown). A decline conveyor 14 is provided wherein the decline conveyor 14 may be alternately turned on and off such that refrigerators housed in shipping containers 12 on the decline conveyor 14 may be alternately urged forward in the direction indicated by arrows 16 or held stationary. A controller 18, which may consist of an IBM 7532 computer system, for example, controls the operation of the system. A photo eye 20 is provided for sending a signal to the controller 18 indicating the presence of a shipping container such that the controller 18 may control the operation of the decline conveyor 14 to ensure adequate spacing between shipping containers. A belt conveyor 22 receives the shipping containers from the decline conveyor 14 and continuously urges the shipping containers 12 onto conveyor rollers 24 while a second photo eye 26 provides indication to the controller 18 when a shipping container is being urged onto the conveyor rollers 24. A probe assembly is shown generally at 28 and may be used for sampling air from within the shipping container 12 as will be described in greater detail.

An air contamination detecting means or gas analyzer 30 is provided for detecting the presence of refrigerant air contaminants indicative of a leak in the sealed refrigeration system. The gas analyzer must be able to discriminate between the presence of refrigerant air contaminants indicative of a refrigerant leak and blowing agent air contaminants which may be the result of outgassing from the foam insulation typically used in the insulation of a refrigeration product. Typically, refrigerants are HFC's or HCFC's such as Freon R12 or R134a and blowing agents are HCFC's or HFC's such as Freon R11 or R141b. As contemplated by the inventor, an embodiment of the air contaminant detection means may be a Micromass instrument from Fisons Instruments Inc. This instrument functions as a tunable mass spectrometer combined with a vacuum system. A display monitor 31 may be provided for graphically displaying the results of the gas analysis as is well-known in the art. As described, the air contaminant detection system is sensitive to refrigerant concentrations as small as 1 part per million.

Figure 2:
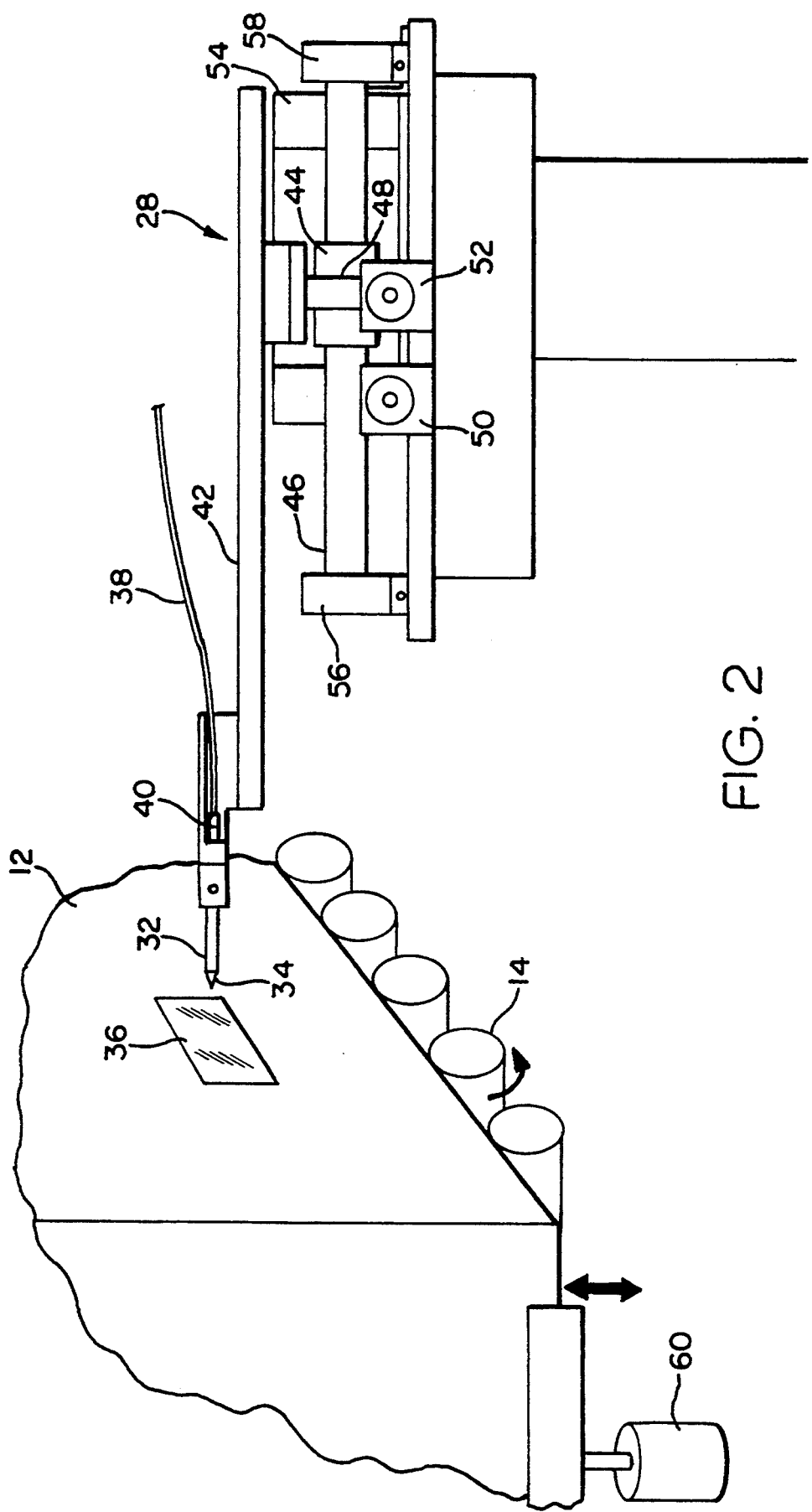
FIG. 2 is a side elevational view of a partially cutaway refrigerator shipping container and assembly of the present invention.

The probe assembly 28 and related elements may be seen in greater detail in FIG. 2. The probe assembly includes a probe 32 consisting of a cylindrical member having a pointed or piercing end 34. The pointed end 34 is suitable for puncturing a reflective film patch 36. The reflective film patch is disposed over and completely covers an opening (not shown) provided in the shipping container 12. A flexible conduit 38 sealably interconnects a second end 40 of the probe 32, opposite the pointed end 34, with the gas analyzer 30. A support member 42 is provided for supporting and extending the probe 32 near the film patch 36. The support member 42 interconnects with a carriage member 44 having internal ball bearings for allowing movement of the carriage member 44 along a travel bar 46. Extending from the carriage member 44 is a flag element 48 for triggering first and second proximity sensors 50 and 52. The proximity sensors 50 and 52 may each be of the type known with the industry as MicroSwitch #923AA3XM-A7T-L.

An electro-solenoid 54 interconnects with the carriage member 44 such that energizing the electro-solenoid 54 causes the carriage member 44 to travel along the travel bar 46 toward a first travel bar support element 56. This movement of the carriage member 44 causes the probe 32 to move toward and puncture through the film patch 36. The travel of the probe 32 is limited such that the probe 32 punctures the film patch 36 but does not contact the exterior cabinet wall (not shown) of the refrigerator disposed within the shipping container 12. Upon deenergizing the electro-solenoid 54, the carriage member 44 is pulled back toward a second travel bar support element 58. At full extension of the carriage member 44 toward the first travel bar support element 56, the flag element 48 triggers the first proximity sensor 50. Upon retraction of the carriage member 44 toward the second travel bar support element 58, the flag element 48 triggers the second proximity sensor 52.

Referring now to both FIG. 1 and FIG. 2, it can be seen that during operation, in response to the urgings of the belt conveyor 22, a shipping container 12 may be urged onto the conveyor rollers 24. When the second photo eye 26 indicates that a shipping container is being urged onto the conveyor rollers 24, the controller 18 verifies that the probe 32 is retracted from inputs from the proximity sensors 50 and 52. In response to the urgings of the conveyor rollers 24, the shipping container 12 moves toward a bar stop assembly 60. The controller 18 raises the bar stop assembly 60 such that the shipping container 12 is held fixed in front of the probe 32 for a predetermined period of time. The presence of the reflective film patch 36 in front of the probe is verified by an optical sensor 62 such that when the controller 18 receives an input from the optical sensor 62 indicating the presence of the reflective film patch 36, the electro-solenoid 54 is activated such that the probe 32 is forcibly inserted into the interior of the shipping container through the reflective film patch 36. The film patch 36 is fabricated from material that allow it to be readily punctured by the probe 32.

Upon insertion of the probe 32 into the shipping container 12, the controller 18 directs the gas analyzer 30 to draw in a sample of air through the probe 32 from the interior of the shipping container. After a predetermined time, the electro-solenoid 54 is deactivated such that the probe 32 is withdrawn from the interior of the shipping container 12. The controller 18 then lowers the bar stop assembly 60 to permit movement of the shipping container 12. The shipping container 12 therefore moves forward due to the urging of the conveyor rollers 24 and is subsequently sorted in response to any detection of air contaminants by the gas analyzer 30.

Upon completion of the contaminant detection operation, a curved conveyor 64 receives the shipping containers from the conveyor rollers 24. Photo eyes 66 and 68 are provided to detect the presence of shipping containers on the curved conveyor 64. A transfer conveyor 70 receives the shipping conveyor from the curved conveyor 64. The sorting of the shipping containers in response to a positive detection of a vaporized refrigerant occurs as the shipping container reaches the transfer conveyor 70.

Incorporated into the transfer conveyor 70 is a pop-up conveyor 72 which is a well known configuration for those skilled in the art. A bar stop 74 is provided for blocking the movement of a shipping container traveling at the urging of the transfer conveyor 70 and a photo eye 76 is provided for detecting when the shipping containers traveling on the transfer conveyor 70 have passed by the bar stop 74. If an air contaminant indicating a refrigerant leak is detected, the controller 18 operates the bar stop 74 to prevent the shipping container from traveling onto a final conveyor 78 and raises the pop-up conveyor 72 such that the shipping container is diverted onto a repair bay conveyor 80 such that the refrigerator having a refrigerant leak may be repaired. In operation, when a refrigerator having a refrigerant leak is detected, the bar stop assembly 60 remains raised until photo eyes 66, 68 and 76 indicate that the curved conveyor 64 and the transfer conveyor 70 are cleared of preceding shipping containers. When all preceding shipping containers have cleared the bar stop 74, the bar stop assembly 60 is retracted allowing the shipping container containing a refrigerator having a refrigerant leak to travel to the bar stop 74 wherein it is diverted onto repair bay conveyor 80.

Figure 3A:
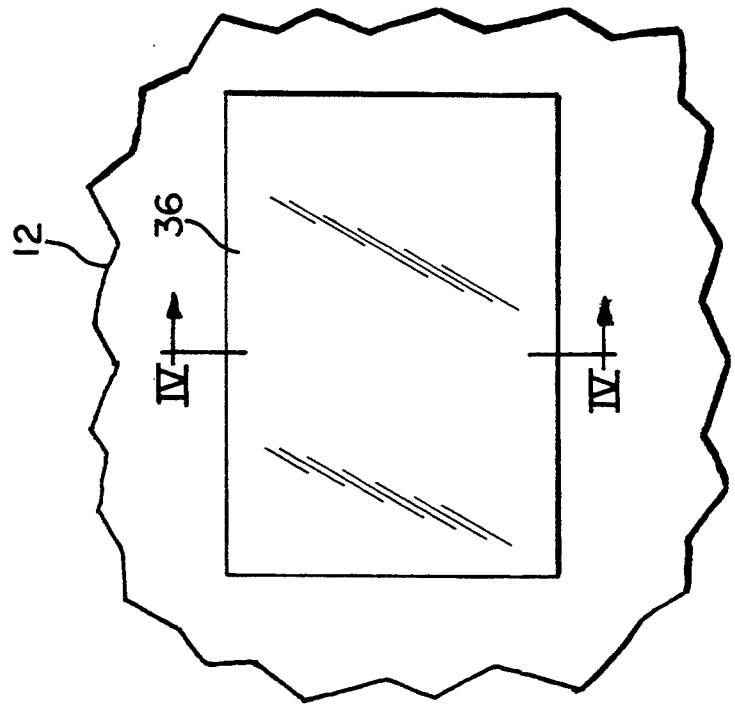
FIG. 3A is a front elevational view of an embodiment of a film patch of the present invention.
Figure 3B:
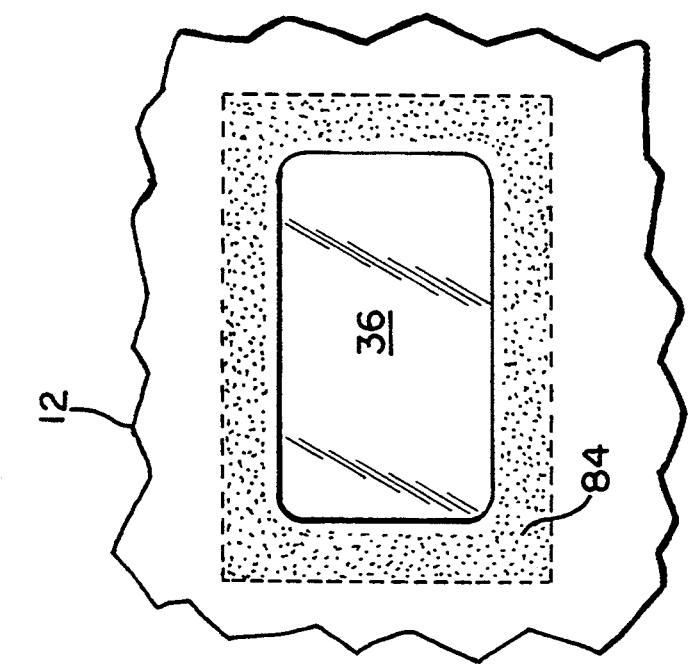
FIG. 3B is a rear elevational view of the film patch as shown in FIG. 3A.
Figure 4:
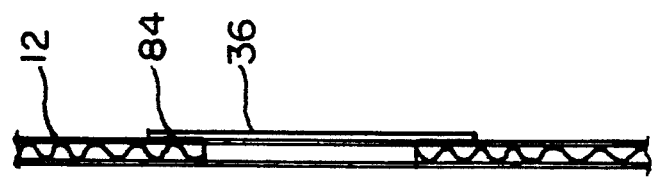
FIG. 4 is a sectional view of a film patch of the present invention taken along a line IV—IV of FIG. 3A.

FIGS. 3A, 3B and FIG. 4 provide details of the reflective film patch 36. FIG. 3A shows the film patch 36 mounted on a shipping container 12 from a front side. FIG. 3B shows the film patch of FIG. 3A from the back side. Adhesive 84 is shown disposed around the periphery of the back side of the film patch 36 for sealably bonding with the portion of the shipping container surrounding the opening provided in the side wall of the shipping container 12. FIG. 4 discloses a sectional view of film patch 36 mounted on shipping container 12.

As is apparent from the foregoing specification, the invention is susceptible of being embodied with various alterations and modifications which may differ particularly from those that have been described in the preceding specification and description. It should be understood that we wish to embody within the scope of the patent warranted hereon all such modifications as reasonably and properly come within the scope of our contribution to the art.

I claim:

1. An apparatus for detecting the presence of a contaminant in the air within an appliance shipping container, said shipping container having at least one wall defining an enclosure surrounding an appliance, said apparatus comprising:
    a probe having an insert end and conduit means;
    means for positioning said shipping container adjacent said insert end of said probe;
    means for inserting said insert end and said conduit means of said probe through said wall;
    an air contaminant detecting means, said air contaminant detecting means interconnected with said conduit means for admitting a test sample of air from within said shipping container to said air contaminant detecting means.

2. The apparatus according to claim 1 wherein said conduit means is contained within said probe and terminates having an open end at said insert end of said probe.

3. The apparatus according to claim 1 further including a flexible conduit connecting said air contaminant detecting means and said conduit means of said probe.

4. The apparatus according to claim 1 wherein said air contaminant detecting means further comprises a tunable mass spectrometer.

5. The apparatus according to claim 4 wherein said tunable mass spectrometer is specifically tuned to detect the presence of vaporized refrigerants in the presence of vaporized blowing agents.

6. The apparatus according to claim 1 wherein said shipping container wall includes a lower portion and said means for inserting said insert end and said conduit means of said probe through said exterior wall of said shipping container is configured to insert said probe into said lower portion of said shipping container.

7. The apparatus according to claim 1 wherein said shipping container further comprises:
    an opening disposed on said shipping container wall such that said means for positioning said shipping container adjacent to said insert end of said probe positions said insert end of said probe adjacent to said opening; and
    a film patch disposed over said opening and sealably adhered to said shipping container wall and pierceable by said probe.

8. The apparatus according to claim 1 wherein said means for positioning said shipping container adjacent said insert end of said probe comprises an assembly line conveyor having a blade stop for stopping said shipping container adjacent said probe.

9. The apparatus according to claim 1 wherein said appliance is a refrigerator.

10. The apparatus according to claim 1 wherein said shipping container includes four side walls, a top and a bottom.

11. The apparatus according to claim 1 wherein said means for inserting said probe further comprises:
    a carriage member for supporting said probe, said carriage being linearly moveable between a first position and a second position;
    a flag element extending from said carriage member;
    a first proximity sensor for detecting the presence of said flag element when said carriage is in said first position;
    a second proximity sensor for detecting the presence of said flag element when said carriage is in said second position; and
    a solenoid actuator assembly interconnected with said carriage for linearly actuating said carriage between said first and second positions.

12. An apparatus according to claim 1 further comprising:
    means for indicating the presence of said contaminant in response to a detection of said contaminant;
    means for causing said shipping container to be sorted in response to the presence of said contaminant.

13. A system for detecting the presence of a leak in a sealed refrigeration system of a refrigerator, said refrigerator being surrounded by a shipping container having a plurality of exterior walls and further having an upper portion and a lower portion, said system comprising:
    a probe having a conduit means;
    a means for positioning said lower portion of said shipping container containing said refrigerator adjacent of said probe;
    means for forcibly inserting said probe through one of said exterior walls;
    an air contaminant detecting means for detecting an air contaminant present upon a leak in said sealed refrigeration system;
    means for interconnecting said probe and said air contaminant detecting means such that a test sample of air from within said shipping container may be admitted to said air contaminant detecting means through said conduit means of said probe;

means for indicating the presence of said contaminant in response to a detection of said contaminant;

means for causing said shipping container to be sorted in response to an presence of said contaminant.

14. A system according to claim 13 further comprising:
    an opening disposed on one of said exterior walls of said shipping container such that said means for positioning said lower portion of said shipping container positions said probe in front of said opening; and
    a film patch disposed over said opening and sealably adhered to said exterior wall of said shipping container such that said means for forcibly inserting said probe through one of said exterior walls of said shipping container forces said probe through said film patch.

15. A system according to claim 13 wherein said air contaminant detecting means comprises a mass spectrometry means for detecting the presence of vaporized refrigerants in the presence of vaporized blowing agents.

16. A system according to claim 13 wherein said means for forcibly inserting said probe through one of said exterior walls further comprises:
    a carriage member for supporting said probe, said carriage being linearly moveable between a first position and a second position;
    a flag element extending from said carriage member;
    a first proximity sensor for detecting the presence of said flag element when said carriage is in said first position;
    a second proximity sensor for detecting the presence of said flag element when said carriage is in said second position; and
    a solenoid actuator assembly interconnected with said carriage for linearly actuating said carriage between said first and second positions.

17. A method for detecting leaks in the sealed system of a refrigerator said refrigerator being disposed within a shipping container having a plurality of exterior walls for creating an enclosure for surrounding said appliance, said method includes the use of a mass spectrometer for identifying the presence of an air contaminant indicative of a leak in the sealed system, said method comprising:
    forming an opening disposed on one of said exterior walls of said shipping container;
    positioning a patch over said opening such that said opening is sealingly covered;
    surrounding said refrigerator with said shipping container;
    inserting a probe into said shipping container through said film patch; and
    drawing a sample of air through said probe into said mass spectrometer such that said leak in said sealed system of said refrigerator within said shipping container may be sensed.

* * * * *